(12) United States Patent
Garrone et al.

(10) Patent No.: US 7,879,836 B2
(45) Date of Patent: Feb. 1, 2011

(54) PHARMACEUTICAL COMPOSITION COMPRISING A 1-(3-CHLOROPHENYL)-3-ALKYLPIPERAZINE FOR TREATING APPETITE DISORDER

(75) Inventors: Beatrice Garrone, Morsasco (IT); Maurizio Magnani, Florence (IT); Guido Furlotti, Rome (IT); Nicola Cazzolla, Albano Laziale (IT); Angelo Guglielmotti, Rome (IT)

(73) Assignee: Aziende Chimiche Riunite Angelini Francesco A.C.R.A.F. S.p.A., Rome (IT)

( * ) Notice: Subject to any disclaimer, the term of this patent is extended or adjusted under 35 U.S.C. 154(b) by 146 days.

(21) Appl. No.: 11/910,559

(22) PCT Filed: Jun. 2, 2006

(86) PCT No.: PCT/EP2006/005390
§ 371 (c)(1),
(2), (4) Date: Apr. 2, 2008

(87) PCT Pub. No.: WO2006/136284
PCT Pub. Date: Dec. 28, 2006

(65) Prior Publication Data
US 2009/0054461 A1   Feb. 26, 2009

(30) Foreign Application Priority Data
Jun. 24, 2005   (IT) .......................... MI2005A1193

(51) Int. Cl.
*A61K 31/4965* (2006.01)
(52) U.S. Cl. .................... 514/183; 514/255.03
(58) Field of Classification Search .................. None
See application file for complete search history.

(56) References Cited

U.S. PATENT DOCUMENTS

| | | | |
|---|---|---|---|
| 3,253,989 A | 5/1966 | Moser et al. | |
| 3,637,705 A | 1/1972 | Horrom et al. | |
| 3,929,792 A | 12/1975 | Bouchara | |

FOREIGN PATENT DOCUMENTS

WO   WO 93/14091   7/1993

OTHER PUBLICATIONS

Sugimoto et al (Biol Pharm Bull 24:1431-1433, 2001).*
Williams et al (Foye's Principles of Medicinal Chemistry, 5th Edition, pp. 59-61, 2002).*
Giannangeli et al (J Med Chem 42:336-345, 1999).*
G.A. Kennett, et al., "5-$HT_{1B}$ Agonists Induce Anorexia at a Postsynaptic Site", European Journal of Pharmacology, vol. 141, 1987, pp. 429-435.
G.A. Kennett, et al., "Anxiogenic-Like Effects of mCPP and TFMPP in Animal Models are Opposed by 5-$HT_{1C}$ Receptor Antagonists", European Journal of Pharmacology, vol. 164, 1989, pp. 445-454.
D.L. Murphy, et al., "III. Serotonin-Selective Arylpiperazines with Neuroendocrine, Behavioral, Temperature, and Cardiovascular Effects in Humans", Pharmacological Reviews, vol. 43 No. 4, 1991, pp. 527-552.
René S. Kahn, et al., "m-Chlorophenylpiperazine as a Probe of Serotonin Function", BIOL Psychiatry, vol. 30, 1991, pp. 1139-1166.
John H. Krystal, et al., "m-Chlorophenylpiperazine Effects in Neuroleptic-Free Schizophrenic Patients", Arch. Gen. Psychiatry, vol. 50, Aug. 1993, pp. 624-635.
Pedro Delgado, "Euphorogenic Properties of the Serotonergic Partial Agonist m-Chlorophenylpiperazine in Cocaine Addicts", Arch. Gen. Psychiatry, vol. 50, Dec. 1993, p. 1001.
John H. Krystal, et al., "Specificity of Ethanollike Effects Elicited by Serotonergic and Noradrenergic Mechanisms", Arch. Gen. Psychiatry, vol. 51, Nov. 1994, pp. 898-911.
M. Giannangeli, et al., "Effect of Modifications of the Alkylpiperazine Moiety of Trazodone on 5-$HT_{2A}$ and $a_1$ Receptor Binding Affinity" Journal of Medicinal Chemistry, vol. 42, No. 3, 1999, pp. 336-345.

* cited by examiner

*Primary Examiner*—Brandon J Fetterolf
*Assistant Examiner*—Craig Ricci
(74) *Attorney, Agent, or Firm*—Oblon, Spivak, McClelland, Maier & Neustadt, L.L.P.

(57) ABSTRACT

Use of a 1-(3-chlorophenyl)-3-alkylpiperazine of formula (I), in racemic (R,S) form or in the form of the (S) enantiomer, in which R is a linear or branched alkyl group having from 1 to 3 carbon atoms, or of an addition salt thereof with a pharmaceutically acceptable organic or inorganic acid, for treating appetite disorder. A pharmaceutical composition that comprises a therapeutically effective amount of a 1-(3-chlorophenyl)-3-alkylpiperazine of formula (I) as previously defined or of an addition salt thereof with a pharmaceutically acceptable organic or inorganic acid, and at least one pharmaceutically acceptable excipient.

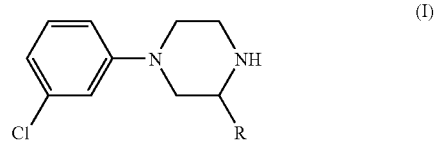

(I)

8 Claims, 1 Drawing Sheet

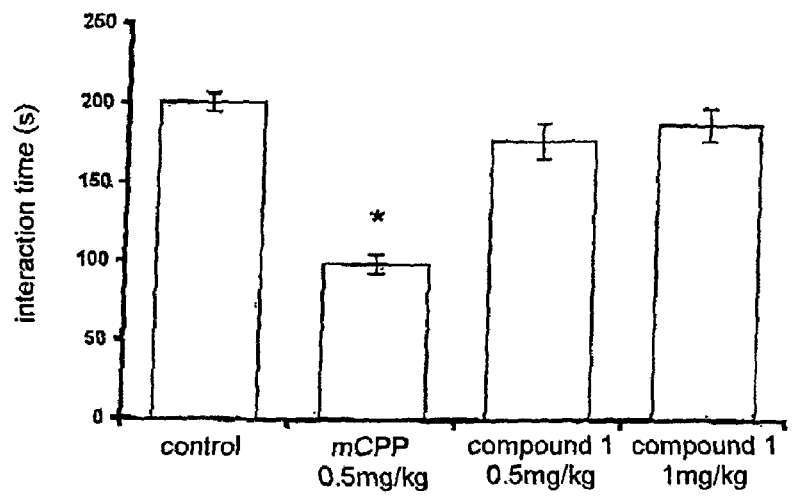
Fig. 1. Anxiogenic effect
10 pairs of rats/group; mean±SEM: *p<0.05 vs. control. ANOVA followed by Dunnett's test
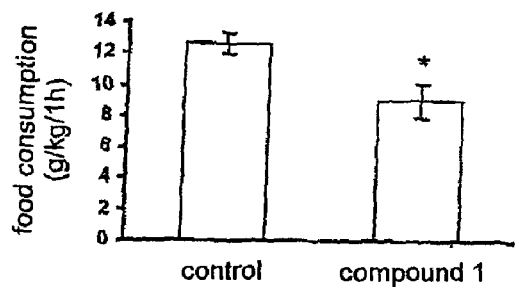
Fig. 2A
Hypophagia-inducing effect of compound 1
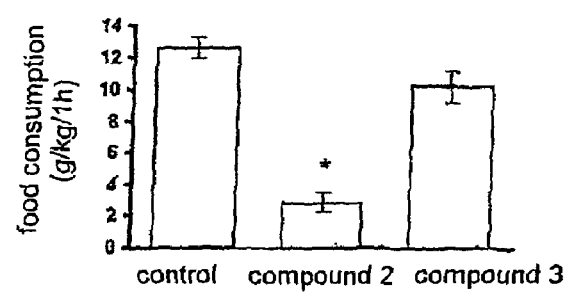
Fig. 2B
Hypophagia-inducing effect of compounds 2 and 3
10 rats/group; mean±SEM;*p<0.05 vs. control. ANOVA followed by Dunnett's test

PHARMACEUTICAL COMPOSITION COMPRISING A 1-(3-CHLOROPHENYL)-3-ALKYLPIPERAZINE FOR TREATING APPETITE DISORDER

The present invention relates to the pharmaceutical use of a 1-(3-chlorophenyl)-3-alkylpiperazine having a chiral centre (S) and of pharmaceutically acceptable acid addition salts thereof.

More particularly, the present invention relates to the use of a 1-(3-chlorophenyl)-3-alkylpiperazine having a chiral centre (S) and of pharmaceutically acceptable acid addition salts thereof in the treatment of appetite disorders.

Throughout the present description and the claims, the expression "having a chiral centre (S)", where used, is intended to refer both to the racemic product (R,S) and to the single (S) enantiomer.

U.S. Pat. No. 3,253,989 describes an N-phenylpiperazine of formula

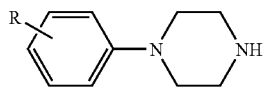

in which R is H, m-Cl, p-Cl, m-CH3 or p-CH3,
endowed with anorexigenic activity.

Furthermore, other N-phenylpiperazines endowed with hypophagia-inducing activity are described in the literature, for example m-trifluoromethyl phenylpiperazine (TFMPP) (Eur J Pharmacol, 1987; 141: 429).

However, use of the N-phenylpiperazines is limited by CNS side-effects which cause changes in mood and behaviour leading to induction of anxiety states which often result in panic attacks. Experimental studies have clearly demonstrated anxiogenic effects of compounds such as m-chlorophenyl-piperazine (mCPP) and TFMPP which reduce social interaction time in the rat (Eur J Pharmacol, 1989; 164: 445-54). Moreover, it has been demonstrated that mCPP induces and/or aggravates panic attacks in patients with anxiety, obsessions in patients with obsessive-compulsive disorder, states of euphoria in alcoholics and cocaine addicts and the symptomatology of schizophrenic patients (Pharmacol Rev, 1991; 43: 527; Biol Psychiatr, 1991; 30: 1139; Arch Gen Psychiatr, 1993; 50: 624; Arch Gen Psychiatr, 1993; 50: 1001; Arch Gen Psychiatr, 1994; 51: 898).

These severe side-effects of the phenylpiperazines represent a serious drawback in chronic pathologies that are very important from the social standpoint, for example obesity. In fact, obesity can be regarded as a chronic pathological condition, resulting from complex interactions of cultural, psychological and genetic factors.

Obesity is defined in terms of BMI (Body Mass Index) calculated as weight (kg)/[height (m)]$^2$. Currently, a BMI below 25 is considered normal, from 25 to 29.9 is considered overweight, whereas a BMI above 30 is an indicator of obesity.

One of the commonest causes of an overweight condition and of obesity is an excessive calorie intake which is not utilized by the body, but is accumulated in the adipose tissue.

Once the mass of adipose tissue has accumulated, its reduction is impeded by a complex series of superimposed neuroendocrine systems. This counter-regulatory mechanism, which probably develops as protection against food deprivation and against fetal or neonatal weight loss, causes changes in appetite and in metabolism which makes deliberate weight loss difficult to achieve.

Over recent decades, the prevalence of obesity has increased exponentially, reaching epidemic proportions in Europe and the USA. Recent estimates suggest that, despite the continuing efforts of the public health services, the health problems of overweight and obese subjects are continuing to increase. It has been calculated that the number of obese adults in the 7 major markets (USA, France, Germany, Italy, Spain, Great Britain and Japan) is destined to increase from 95 million in 2000 to 139 million in 2010. Fewer than 25% of potential patients are diagnosed as obese and fewer than 20% of them are treated with drug therapy.

This low percentage of patients receiving drug therapy is due to the limited efficacy of the available drug therapies. Thus, the drugs currently available only succeed in producing a 5-10% initial weight loss in less than 50% of patients treated.

Consequently, the need for an effective drug therapy has increased considerably in the last 30 years, also on account of the social costs associated with obesity. In fact, numerous studies have shown that being overweight greatly increases the risk of morbidity caused by various conditions including diabetes, hypertension, dyslipidaemia, coronary cardiopathies, congestive heart failure and myocardial infarction. Moreover, increased body weight is also often associated with a general increase in mortality.

WO 93/14091 describes a 1-(3-chlorophenyl)-3-alkylpiperazine of formula (I):

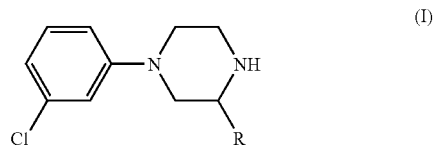

where R is an alkyl group having from 1 to 3 carbon atoms, as an intermediate for preparing alkyl derivatives of trazodone.

M. Giannageli et al. "Effect of Modifications of the Alkylpiperazine Moiety of Trazodone on 5-HT$_2$A and α$_1$ Receptor Binding Affinity" Journal of Medicinal Chemistry 1999, Vol. 42: 336-345, describe a method of separating the two S and R enantiomers of the compound of formula (I) in which R is methyl with (+) and (−)-tartaric acid respectively. Furthermore, those authors also describe the stereospecific synthesis of the (S) enantiomer of the compound of formula (I) in which R is methyl.

To date, however, no therapeutic activity of the compounds of formula (I) had ever been described.

It has now been found that the 1-(3-chlorophenyl)-3-alkylpiperazine of formula (I) having an (S) chiral centre, both as racemic (R,S) and as single (S) enantiomer, is active in the treatment of appetite disorders and is surprisingly without anxiogenic side-effects.

Moreover, even more surprisingly, it has been found that it is mainly the enantiomer of (S) configuration that possesses these properties.

BRIEF DESCRIPTION OF THE DRAWINGS

FIG. 1 presents the results of anxiogenic activity in the rat described in part 2 of the Examples and show the interaction time of the animals treated with the compound of the invention.

FIG. 2 presents the result of hypophagia-inducing activity in food-deprived rats. FIG. 2A shows that the amount of food consumed by the animals treated with the racemic compound (compound 1) of the invention is approx. 28% lower than that consumed by the control animals. FIG. 2B shows that the amounts of food consumed by the animals treated with the (S) enantiomer (compound 2) and with the (R) enantiomer of the invention are approx. 75-80% and 20% lower, respectively, than that consumed by the control animals.

A first aspect of the present invention therefore relates to the pharmaceutical use of a 1-(3-chlorophenyl)-3-alkylpiperazine of formula (I), in racemic (R,S) form or in the form of the (S) enantiomer,

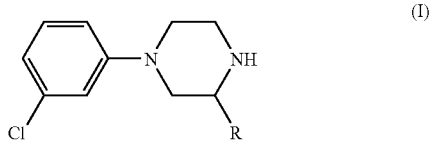

(I)

in which

R is a linear or branched alkyl group having from 1 to 3 carbon atoms, or of an addition salt thereof with a pharmaceutically acceptable organic or inorganic acid.

Preferably, this pharmaceutical use comprises the treatment of an appetite disorder.

Typically, said appetite disorder is selected from the group comprising hyperphagia, bulimia and obesity.

A second aspect of the present invention relates to a pharmaceutical composition that includes a therapeutically effective amount of a 1-(3-chlorophenyl)-3-alkylpiperazine of formula (I), in (R,S) racemic form or in the form of (S) enantiomer,

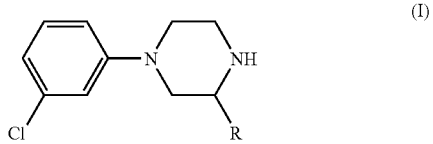

(I)

in which

R is a linear or branched alkyl group having from 1 to 3 carbon atoms, or of an addition salt thereof with a pharmaceutically acceptable organic or inorganic acid, and at least one pharmaceutically acceptable excipient.

Preferably R is methyl or ethyl. Even more preferably, R is methyl.

Advantageously, the compound of formula (I) is an enantiomer of (S) configuration.

Typically, said organic acid is selected from the group comprising maleic, methanesulphonic, paratoluenesulphonic, succinic and citric acid.

In its turn, said inorganic acid is typically selected from the group comprising hydrochloric, hydrobromic, phosphoric and sulphuric acid.

The preferred acid is hydrochloric acid.

In the case of the compound of formula (I) in the (S) configuration, it is also possible to use optically active acids such as lactic acid and tartaric acid, both in the natural L(+) form. In that case, the preferred acid is L(+) tartaric acid.

The compound of formula (I) in racemic (R,S) form can be prepared by known techniques, for example reaction scheme 3 described in WO 93/14091.

The enantiomer in the (S) configuration can also be obtained by known techniques, for example those described by M. Giannangeli et al. (loc. cit.).

The anxiogenic activity of the compounds of the present invention was investigated by means of the social interaction test in the rat, which, as is known by a person skilled in the art, represents an experimental model that is predictive of the effects in humans.

The normal social interaction of rats (sniffing, nipping, grooming) is generally suppressed when the animals are put in an unfamiliar environment. Measurement of the time spent by pairs of animals in interacting with one another and exploring their surroundings (usually an arena consisting of a Perspex container) constitutes a model for verifying the action of substances that influence social behaviour. As is well known, the social interaction test shows numerous similarities between the behaviour exhibited by the rats and anxiety states in humans and proves to be a useful tool for demonstrating effects on mood, both of the anxiogenic and of the anxiolytic type.

The hypophagia-inducing activity of the compounds of formula (I) was demonstrated by verifying the food consumption of food-deprived rats.

As is known to a person skilled in the art, the aforesaid experimental model can also be regarded as predictive of the activity in humans.

Verification of the consumption of food in food-deprived rats represents a condition that reproduces the complex system regulating the sensation of hunger and the intake of food in humans. Fasting in fact introduces many physiological changes that can lead to activation of the circuits that are specifically dedicated to the control of food intake. As is well known, the use of this model constitutes a valid tool for identifying substances capable of interfering with appetite disorders and can be used in particular for monitoring conditions such as hyperphagia, bulimia and obesity.

Preferably the pharmaceutical compositions of the present invention are prepared as suitable dosage forms containing an effective dose of at least one compound of formula (I) or of a pharmaceutically acceptable salt thereof with an organic or inorganic acid and at least one pharmaceutically acceptable inert ingredient.

Examples of suitable dosage forms are tablets, capsules, coated tablets, granules, solutions and syrups for oral administration; medicated patches for transdermal administration; suppositories for rectal administration, and injectable sterile solutions.

Other suitable dosage forms are those with extended release and those based on liposomes, for administration by the oral, injectable or transdermal route.

The dosage forms can also contain other conventional ingredients such as: preservatives, stabilizers, surfactants, buffers, salts for regulating osmotic pressure, emulsifiers, sweeteners, colorants, flavourings and the like.

If required for particular therapeutic requirements, the pharmaceutical composition of the present invention can contain other pharmacologically active ingredients, whose concomitant administration is useful.

The amount of compound of formula (I) or of a pharmaceutically acceptable acid addition salt thereof in the pharmaceutical composition of the present invention can vary over a wide range depending on known factors, for example the type of pathology, the severity of the disease, the patient's body weight, the dosage form, the chosen route of administration, the number of daily doses and the efficacy of the chosen compound of formula (I). However, determination of the optimum amount is a simple and routine matter for a person skilled in the art.

Typically, the amount of compound of formula (I) or of a pharmaceutically acceptable acid addition salt thereof in the pharmaceutical composition of the present invention will be such as to ensure a level of administration between 0.001 and 100 mg/kg/day. Preferably the level of administration is between 0.05 and 50 mg/kg/day, and even more preferably between 0.1 and 10 mg/kg/day.

The dosage forms of the pharmaceutical composition of the present invention can be prepared by techniques that are well known to a pharmaceutical chemist, and include mixing, granulation, compression, dissolution, sterilization and the like.

EXPERIMENTAL SECTION

1. Preparation

The compounds of the present invention can be prepared by methods that are known to a person skilled in the art.

Referring to Table 1 below, the racemic compound 1 was prepared by the method described in Example 4 of WO 93/14091 whereas the two enantiomers 2 and 3 were separated with (+) and (−)-tartaric acid respectively, as described by M. Giannangeli et al. (loc. cit.).

The aforesaid methods can also be used for preparing the compounds of the present invention in which R is ethyl or propyl.

The m-chlorophenyl-piperazine (mCPP), used as comparison compound, was prepared by the method described in U.S. Pat. No. 3,253,989.

TABLE 1

| Compound No. | Structure | Configuration |
|---|---|---|
| 1 | (3-Cl-phenyl)-piperazine with CH$_3$ | R,S |
| 2 | (3-Cl-phenyl)-piperazine with CH$_3$ | S |
| 3 | (3-Cl-phenyl)-piperazine with CH$_3$ | R |

2. Anxiogenic Activity in the Rat (Test of Social Interaction)

Male CD rats weighing 150-250 g were used.

The animals were kept in a room with a controlled cycle of light and darkness (6:00-18:00). To promote acclimatization and eliminate responses induced by stress conditions, the rats were handled and were injected daily with the vehicle (water) for the four days preceding administration of the test compounds.

On the fifth day the animals were treated intraperitoneally with the test compounds and, after 20 minutes, the interaction time (seconds) spent by the animals during a 10-minute period was evaluated.

The results are presented in FIG. 1 and show that the interaction time of the animals treated with the compound of the invention is approx. 90-95% of that of the control animals (injected with water only or not treated) whereas the interaction time of the animals treated with the comparison compound (mCPP) is approx. 50% of that of the control animals.

This test therefore demonstrates that the compounds of the present invention are almost devoid of anxiogenic activity.

Similar results can be obtained with the compounds of the invention in which R is ethyl or propyl.

3. Hypophagia-inducing Activity in Food-deprived Rats

Male CD rats weighing 300-350 g were used.

The animals were kept in a room with a controlled cycle of light and darkness (6:00-18:00). Before the test, which was carried out at 9:30 corresponding to daytime, the animals were deprived of food for 24 h. At the end of the fasting period, the animals were treated orally with the test compounds (10 mg/kg) in an aqueous vehicle and, immediately after treatment, a pre-weighed amount of food was made available. One hour after treatment, the food consumption was evaluated by weighing the amount of food remaining. The control animals were treated orally with the vehicle (water) used for administering the test compounds.

The results are shown in FIGS. 2A and 2B.

FIG. 2A shows that the amount of food consumed by the animals treated with the racemic compound (compound 1) of the invention is approx. 28% lower than that consumed by the control animals. In its turn, FIG. 2B shows that the amounts of food consumed by the animals treated with the (S) enantiomer (compound 2) and with the (R) enantiomer of the invention are approx. 75-80% and 20% lower, respectively, than that consumed by the control animals.

FIG. 2B therefore shows that the hypophagia-inducing activity of the racemic compound of the invention can be attributed almost entirely to the (S) enantiomer.

Similar results can be obtained with the compounds of the invention in which R is ethyl or propyl.

4. Pharmaceutical Compositions

4.1 Tablet

A tablet containing a compound of the present invention as active principle has the following composition:

| | |
|---|---|
| Active principle | 50 mg |
| Lactose monohydrate | 161 mg |
| Dibasic calcium phosphate dihydrate | 161 mg |
| Microcrystalline cellulose | 95 mg |
| Maize starch | 30 mg |
| Sodium carboxymethylamide | 24 mg |
| Povidone | 11 mg |
| Magnesium stearate | 3 mg |

4.2 Injectable Solution

A vial contains 5 ml of an injectable solution containing a compound of the present invention as active principle.

Said solution has the following composition:

| | |
|---|---|
| Active principle | 25 mg |
| Sorbitol | q.s.f. isoosmotic solutions |
| Sterile water for injection | q.s.f. 5 ml |

4.3 Granules

A sachet contains 5.23 g of water-dispersible granules containing a compound of the present invention as active principle. Said granules have the following composition:

| | |
|---|---|
| Active principle | 50 mg |
| Maltitol | 1300 mg |
| Mannitol | 2700 mg |
| Sucrose | 1000 mg |
| Citric acid | 15 mg |
| Aspartame | 15 mg |
| Flavourings | 150 mg |

The invention claimed is:

1. A method for the treatment of hyperphagia comprising the administration to a patient in need thereof of a pharmaceutical composition comprising a therapeutically effective amount of a 1-(3-chlorophenyl)-3-alkylpiperazine of formula (I), in racemic (R,S) form or in the form of the (S) enantiomer,

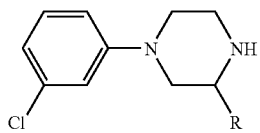

(I)

in which

R is a linear or branched alkyl group having from 1 to 3 carbon atoms, or of an addition salt thereof with a pharmaceutically acceptable organic or inorganic acid, and at least one pharmaceutically acceptable excipient.

2. The method according to claim 1, wherein R is methyl or ethyl.

3. The method according to claim 1, characterized in that wherein R is methyl.

4. The method according to any one of the preceding claims, wherein the compound of formula (I) is an enantiomer of (S) configuration.

5. The method according to any one of the preceding claims, wherein said organic acid is selected from the group consisting of maleic, methanesulphonic, paratoluenesulphonic, succinic and citric acid.

6. The method according to any one of the claims from 1 and 2 to 4, wherein said inorganic acid is selected from the group consisting of hydrochloric, hydrobromic, phosphoric and sulphuric acid.

7. The method according to any one of the claims from 1 and 2 to 4, wherein said acid is hydrochloric acid.

8. The method according to claim 4, wherein said acid is selected from the group comprising L(+) lactic and L(+) tartaric acid.

\* \* \* \* \*